United States Patent [19]

Bays et al.

[11] Patent Number: 4,839,377
[45] Date of Patent: Jun. 13, 1989

[54] 5-SUBSTITUTED 3-AMINOALKYL INDOLES

[75] Inventors: David E. Bays, Ware; Colin F. Webb, Royston; Michael D. Dowle, Ware, all of United Kingdom

[73] Assignee: Glaxo Group Limited, London, England

[21] Appl. No.: 82,132

[22] Filed: Aug. 6, 1987

Related U.S. Application Data

[63] Continuation of Ser. No. 711,152, Mar. 13, 1985, abandoned, which is a continuation of Ser. No. 431,597, Sep. 30, 1982, abandoned, which is a continuation of Ser. No. 292,023, Aug. 11, 1981, abandoned.

[30] Foreign Application Priority Data

Aug. 12, 1980 [GB] United Kingdom ................. 8026287

[51] Int. Cl.⁴ ..................... A61K 31/40; C07D 209/16
[52] U.S. Cl. .................................... 514/415; 514/212; 514/323; 514/414; 540/602; 546/201; 548/468; 548/504
[58] Field of Search ............... 514/414, 415, 323, 212; 546/201; 548/468, 504; 540/602

[56] References Cited

FOREIGN PATENT DOCUMENTS 1203195 1/1960 France .
2211249 7/1974 France .

OTHER PUBLICATIONS

Burger, Medicinal Chemistry, Fourth Edition, Part I, pp. 178–182, John Wiley and Sons, N.Y. (1979), RS 403B8.
Ariens, Drug Design, pp. 10 and 11, vol. II (1971), Academic Press, N.Y. (1971).
L. Greene, Protective Groups in Organic Synthesis pp. 223, 250, 251, 263, John Wiley and Sons (1981) N.Y., QD 262 G665.
I. Coates et al., Chem. Abstracts vol. 97, No. 6148d (1982). Indole derivatives and their medicinal use.

Primary Examiner—Mary E. Ceperley
Attorney, Agent, or Firm—Bacon & Thomas

[57] ABSTRACT

Compounds are disclosed of general formula (I)

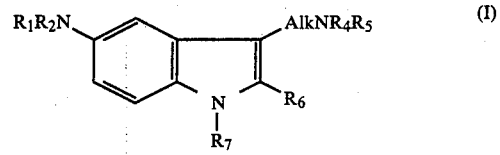

wherein
$R_1$ represents a group CHO, $COR_8$, $CO_2R_8$, $CONR_9R_{10}$, $CSNR_9R_{10}$ or $SO_2NR_9R_{10}$,
where $R_8$ represents an alkyl, cycloalkyl, aryl or aralkyl group,
$R_9$ represents a hydrogen atom or an alkyl group, and
$R_{10}$ represents a hydrogen atom or an alkyl, cyclo-alkyl, aryl or aralkyl group;
$R_2$, $R_3$, $R_4$, $R_6$ and $R_7$, which may be the same or different, each represents a hydrogen atom or a $C_{1-3}$ alkyl group;
$R_5$ represents a hydrogen atom or an alkyl, cycloalkyl, alkenyl or an aralkyl group or
$R_4$ and $R_5$ together form an aralkylidene group or
$R_4$ and $R_5$ together with the nitrogen atom to which they are attached form a saturated monocyclic 5- to 7-membered ring; and
Alk represents an alkylene chain containing two or three carbon atoms which may be unsubstituted or substituted by not more than two $C_{1-3}$ alkyl groups;
with the provisos that when $R_4$ and $R_5$ both represent alkyl groups $R_1$ does not represent the group CHO or $COR_8$ and that when $R_4$, $R_5$, $R_6$ and $R_7$ all represent hydrogen $R_1$ does not represent the group $SO_2NH_2$;
and physiologically acceptable salts, solvates and bioprecursors thereof. The components are described as potentially useful for the treatment of migraine and may be formulated as pharmaceutical compositions in convention manner using one or more pharmaceutically acceptable carriers or excipients. Various processes for the preparation of the compounds are disclosed including, for example, reaction of an aminoalkyl indole with an acid of formula $R_1OH$ or an acylating agent corresponding thereto or with an inorganic cyanate or an organic isocyanate or isothiocyanate in order to introduce the desired $R_1$ group at the 5-position on the indole nucleus.

10 Claims, No Drawings

5-SUBSTITUTED 3-AMINOALKYL INDOLES

This application is a continuation of application Ser. No. 711,152 filed Mar. 13, 1985, which is a continuation of Ser. No. 431,597 filed Sept. 30, 1982, now abandoned, which is a continuation of Ser. No. 292,023 filed Aug. 11, 1981 now abandoned.

This invention relates to heterocyclic compounds, to processes for their preparation, to pharmaceutical compositions containing them and to their medical use.

The present invention provides an indole of the general formula (I):

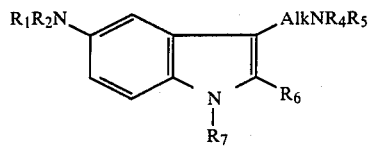

wherein
$R_1$ represents a group CHO, $COR_8$, $CO_2R_8$, $CONR_9R_{10}$, $CSNR_9R_{10}$ or $SO_2NR_9R_{10}$,
where $R_8$ represents an alkyl, cycloalkyl, aryl or aralkyl group;
$R_9$ represents a hydrogen atom or an alkyl group and
$R_{10}$ represents a hydrogen atom or an alkyl, cycloalkyl, aryl or aralkyl group;
$R_2$, $R_4$, $R_6$ and $R_7$, which may be the same or different, each represents a hydrogen atom or a $C_{1-3}$ alkyl group;
$R_5$ represents a hydrogen atom or an alkyl, cycloalkyl, alkenyl or an aralkyl group or
$R_4$ and $R_5$ together form an aralkylidene group or
$R_4$ and $R_5$ together with the nitrogen atom to which they are attached form a saturated monocyclic 5- to 7-membered ring; and
Alk represents an alkylene chain containing two or three carbon atoms which may be unsubstituted or substituted by not more than two $C_{1-3}$ alkyl groups;
with the provisos that when $R_4$ and $R_5$ both represent alkyl groups $R_1$ does not represent the group CHO or $COR_8$ and that when $R_4$, $R_5$, $R_6$ and $R_7$ all represent hydrogen, $R_1$ does not represent the group $SO_2NH_2$;
and physiologically acceptable salts solvates (e.g. hydrates) and bioprecursors thereof.

The compounds according to the invention include all optical isomers thereof and their racemic mixtures.

Referring to the general formula (I) the alkyl groups may be straight chain or branched chain alkyl groups and they preferably contain from 1 to 6 carbon atoms unless otherwise specified. The alkyl groups represented by $R_8$ may be unsubstituted or substituted by one to three halogen atoms e.g. flourine. The cycloalkyl groups preferably contain 5 to 7 carbon atoms. The term aryl, used as such or in the term aralkyl, preferably means phenyl which may be unsubstituted or substituted by one or more alkyl groups e.g. methyl, halogen atoms e.g. flourine, or hydroxy or alkoxy groups e.g. methoxy. The alkyl moiety of the aralkyl groups preferably contains 1 to 4 carbon atoms. The aralkylidene group is preferably an arylmethylidene group. The alkenyl groups preferably contain 3 to 6 carbon atoms.

Suitable physiologically acceptable salts of the indoles of general formula (I) include acid addition salts formed with organic or inorganic acids for example hydrochlorides, hydrobromides, sulphates, fumarates and maleates. Other salts may be useful in the preparation of compounds of formula (I) e.g. creatinine sulphate adducts.

The term "bioprecursors" used herein means compounds which have a structure different from that of the compound of formula (I) but which, upon administration to an animal or human being, are converted in the body to a compound of formula (I).

The compounds of the invention mimic methysergide in contracting the dog, isolated saphenous vein strip (E. Apperley et al., Br. J. Pharmacol., 1980, 68, 215–224) and, like methysergide, they have little effect on blood pressure in the DOCA Hypertensive rat. Methysergide is known to be useful in the treatment of mirgraine and produces a selective increase in carotid vascular resistance in the anaesthetised dog; it has been suggested (P. R. Saxena., Eur. J. Pharmacol, 1974, 27, 99–105) that this is the basis of its efficacy. Those compounds which we have tested show a similar effect in the anaesthetised dog and the compounds according to the invention are thus potentially useful for the treatment of migraine.

Accordingly, the invention also provides a pharmaceutical composition adapted for use in human medicine which comprises at least one compound of general formula (I), a physiologically acceptable salt, solvate (e.g. hydrate) or a bioprecursor thereof and formulated for administration by any convenient route. Such compositions may be formulated in conventional manner using one or more pharmaceutically acceptable carriers or excipients.

Thus, the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The compounds of the invention may be formulated for parenteral administration by injection, including using conventional catheterisation techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral or buccal administration to man for the treatment of migraine is 0.1 to 100 mg of the active ingredient per unit dose which could be administered, for example 1 to 4 times per day.

Aerosol formulations are preferably arranged so that each metered dose or "puff" of aerosol contains 20 μg–1000 μg of the compound of the invention. The overall daily dose with an aerosol will be within the range 100 μg–10 mg. Administration may be several times daily, for example 2, 3, 4 or 8 times, giving for example 1, 2 or 3 doses each time. The overall daily dose and the metered dose delivered by capsules and cartridges in an inhaler or insufflator could be double those with aerosol formulations.

A preferred class of compounds represented by the general formula (I) is that wherein Alk represents an unsubstituted alkylene chain containing two carbon atoms. Another preferred class of compounds of general formula (I) is that wherein $R_4$ and $R_5$ each represents a hydrogen atom or a methyl or ethyl group and $R_6$ and $R_7$ each represents a hydrogen atom. It is preferred that the total number of carbon atoms in $R_4$ and $R_5$ together does not exceed two.

A further preferred class of compounds of general formula (I) is wherein
$R_2$ represents a hydrogen atom or a methyl group.

A preferred class of compounds according to the invention is represented by the general formula (Ia):

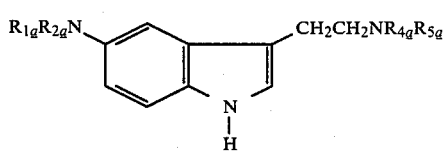

wherein
$R_{1a}$ represents a group CHO, CONH$_2$, COR$_{8a}$ or CO$_2$R$_{8a}$, where $R_{8a}$ is an alkyl group containing 1 to 4 carbon atoms, e.g. a methyl, ethyl or isobutyl group, or a trifluoromethyl group;
$R_{2a}$ represents a hydrogen atom or a methyl group; and
$R_{4a}$ and $R_{5a}$, which may be the same or different, each represents a hydrogen atom or a methyl or ethyl group (with the provisos that the total number of carbon atoms in $R_{4a}$ and $R_{5a}$ together does not exceed two and that when $R_{1a}$ represents a group CHO or a group COR$_{8a}$ then $R_{4a}$ represents a hydrogen atom), and physiologically acceptable salts, solvates (e.g. hydrates) or bioprecursors thereof.

A particularly preferred class of compounds according to the invention is represented by the general formula (Ib):

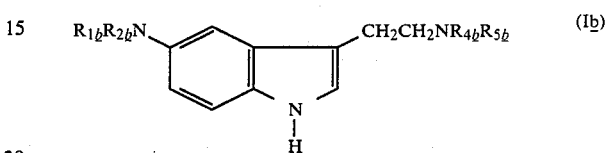

wherein
$R_{1b}$ represents a group CHO, CONH$_2$ or CO$_2$R$_{8b}$ wherein $R_{8b}$ is a methyl, ethyl or isobutyl group;
$R_{2b}$ represents a hydrogen atom or a methyl group; and
$R_{4b}$ and $R_{5b}$, which may be the same or different, each represents a hydrogen atom or a methyl or ethyl group (with the provisos that the total number of carbon atoms in $R_{4b}$ and $R_{5b}$ together does not exceed two and that when $R_{1b}$ is the group CHO, $R_{4b}$ represents a hydrogen atom), and physiologically acceptable salts, solvates (e.g. hydrates) and bioprecursors thereof.

According to another aspect of the invention, compounds of general formula (I) and physiologically acceptable salts, solvates (e.g. hydrates) or bioprecursors thereof, may be prepared by the general methods outlined below. In the following processes, $R_1$, $R_2$, $R_4$, $R_5$, $R_6$, $R_7$ and Alk are as defined for the general formula (I), unless otherwise specified.

According to one general process (A), a compound of general formula (I) may be prepared by reacting a compound of general formula (II);

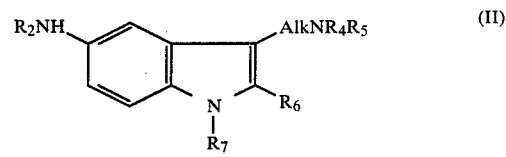

or a protected derivative thereof, with a suitable reagent which serves to introduce the group $R_1$.

Suitable reagents which serve to introduce the group $R_1$ include acids of formula $R_1$OH or acylating agents corresponding thereto, inorganic cyanates, appropriate organic isocyanates or organic isothiocyanates.

Acylating agents which may conveniently be employed in the above process include acid halides (for example acid chlorides and sulphamoyl chlorides), alkyl esters (e.g. the methyl or ethyl ester), activated esters (for example the 2-(1-methylpyridinyl)ester), symmetrical anhydrides or mixed anhydrides, haloformates (e.g. ethylchloroformate) or other activated carboxylic acid derivatives such as those conventionally used in peptide synthesis.

The process may be effected in a suitable aqueous or non-aqueous reaction medium, conveniently at a temperature of from −70° to −150° C. Thus, the process using an activated ester or an anhydride may be effected in a suitable reaction medium such as an amide (e.g. dimethylformamide), an ether (e.g. tetrahydrofuran), a nitrile (e.g. acetonitrile), a haloalkane (e.g. dichloromethane) or a mixture thereof, optionally in the presence of a base, such as pyridine or a tertiary amine such as triethylamine. The reaction is preferably effected at a temperature of from −5° to +25° C.

The reaction using an alkyl ester may be effected in a suitable reaction medium such as an alcohol (e.g. methanol), an amide (e.g. dimethylformamide), an ether (e.g. tetrahydrofuran) or a mixture thereof and conveniently at a temperature of from 0° to 100° C. When the reagent is an inorganic cyanate, an organic isocyanate or an organic isothiocyanate the reaction may be carried out in water, an alcohol (e.g. ethanol), an amide (e.g. dimethylformamide) an ether (e.g. tetrahydrofuran) or a mixture thereof, optionally in the presence of a base such as pyridine or a tertiary amine such as triethylamine and conveniently at a temperature of from 0° to 100° C.

Acids of formula $R_1OH$ may themselves be used in the preparation of compounds of formula (I). The reaction with such an acid is desirably conducted in the presence of a coupling agent, for example carbonyl diimidazole or N,N'-dicyclohexylcarbodiimide. The reaction may be carried out in a suitable reaction medium such as a haloalkane (e.g. dichloromethane), a nitrile (e.g. acetonitrile), an amide (e.g. dimethylformamide) or an ether (e.g. tetrahydrofuran) conveniently at a temperature of from −5° to +30° C. The reaction may also be carried out in the absence of a coupling agent in a suitable reaction medium such as a hydrocarbon (e.g. toluene or xylene) conveniently at a temperature of from 50° to 120° C.

A compound of general formula (I) wherein $R_1$ represents —CHO may be prepared by heating a compound of general formula (II) in formic acid, preferably at reflux.

In a particular embodiment of this process, a compound of formula (I) wherein, $R_1$ represents the group —$CONR_9R_{10}$ or —$CSNR_9R_{10}$, may also be prepared by reaction of a compound of formula (II), or protected derivative thereof, with phosgene or thiophosgene followed by an appropriate amine of formula $R_9R_{10}NH$.

The reaction is conveniently carried out in an inert organic solvent, such as an aromatic hydrocarbon (e.g. toluene).

Some starting compounds of general formula (II) wherein $R_2$ is hydrogen, may be prepared by reduction of a corresponding compound having an appropriate reducible group as the 5-position substituent such as —CN or

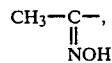

using for example, lithium aluminium hydride.

According to another general process (B), compounds of general formula (I) may be prepared by cyclisation of a compound of general formula (III):

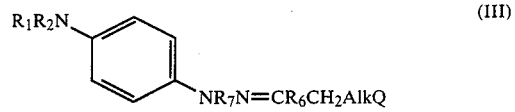

wherein Q is the group $NR_4R_5$ (or a protected derivative thereof) or a leaving group such as halogen (e.g. chlorine), acetate, tosylate or mesylate.

Suitable cyclisation methods are referred to in "A Chemistry of Heterocyclic Compounds — Indoles Part 1", Chapter II, edited by W.J. Houlihan (1972) Wiley Interscience, NY. Particularly convenient embodiments of the process are described below.

When Q is the group $NR_4R_5$ (or a protected derivative thereof), the process is desirably carried out in an aqueous reaction medium, such as an aqueous alcohol (for example methanol) in the presence of an acid catalyst. (In some cases the acid catalyst may also act as the reaction solvent). Suitable acid catalysts include inorganic acids such as sulphuric or hydrochloric acid or organic carboxylic acids such as acetic acid. Alternatively the cyclisation may be carried out in the presence of a Lewis acid such as zinc chloride in ethanol or boron trifluoride in acetic acid. The reaction may conveniently be carried out at temperatures of from 20° to 200° C., preferably 50 ° to 125° C.

When Q is a leaving group such as chlorine, the reaction may be effected in an aqueous organic solvent, such as an aqueous alcohol (e.g. methanol, ethanol or isopropanol), in the absence of a mineral acid, conveniently at a temperature of from 20° to 200° C., preferably 50° to 125° C. This process results in the formation of a compound of formula (I) wherein $R_4$ and $R_5$ are both hydrogen atoms.

According to a particular embodiment of this process compounds of general formula (I) may be prepared directly by the reaction of a compound of general formula (IV):

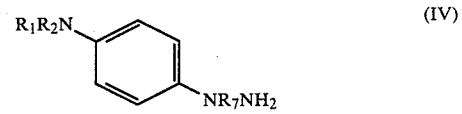

or a salt thereof
with a compound of formula (V)

wherein Q is as defined above or a salt or protected derivative thereof (such as an acetal or ketal e.g. formed with an appropriate alkyl orthoformate), using the appropriate conditions as described above.

Compounds of formula (III) may be isolated as intermediates during the process for the preparation of compounds of general formula (I) wherein a compound of formula (IV), or a salt or protected derivative thereof, is reacted with a compound of formula (V) or a salt or protected derivative thereof, in a suitable solvent, such as an aqueous alcohol (e.g. methanol) and at a temperature of, for example, from 20° to 30° C. If an acetal or ketal of a compound of formula (V) is used, it may be necessary to carry out the reaction in the presence of an acid (for example, acetic or hydrochloric acid). As illustrated in the following general processes (C) and (D), the aminoalkyl substituent —AlkNR$_4$R$_5$ may be introduced at the 3-position by a variety of conventional techniques which may, for example, involve modification of a substituent at the 3-position or direct introduction of the aminoalkyl substituent into the 3-position.

Thus a further general method (C) for preparing compounds of general formula (I) involves reacting a compound of formula (VI):

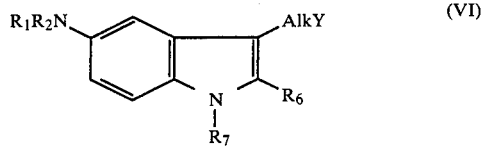

(wherein Y is a readily displaceable group) or a protected derivative thereof, with an amine of formula R$_4$R$_5$NH.

The displacement reaction may conveniently be carried out on those compounds of general formula (VI) wherein the substituent group Y is a halogen atom (e.g. chlorine, bromine or iodine) or a group OR where OR is an acyloxy group, such as acetoxy, chloroacetoxy, dichloroacetoxy trifluoroacetoxy or p-nitrobenzoyloxy or a sulphonate group (e.g. p-toluene sulphonate).

The above reaction is conveniently effected in an organic solvent (optionally in the presence of water), examples of which include alcohols, e.g. ethanol; ethers, e.g. tetrahydrofuran; esters e.g. ethyl acetate; amides e.g. N,N—dimethylformamide; and ketones e.g. acetone, at a temperature of from −10° to +150° C., preferably 20° to 50° C.

The compounds of formula (VI) wherein Y is a halogen atom may be prepared by reacting a hydrazine of general formula (IV) with an aldehyde or ketone (or protected derivative thereof) of general formula (V) in which Q is a halogen atom, in an aqueous alkanol (e.g. methanol) containing an acid (e.g. acetic or hydrochloric acid) or by treating a compound of general formula (VI) wherein Y is a hydroxyl group with the appropriate phosphorous trihalide. The intermediate alcohol where Y is a hydroxyl group may also be used to prepare compounds of formula (VI) wherein Y is the group OR by acylation or sulphonylation with the appropriate activated species (e.g. an anhydride or sulphonyl chloride) using conventional techniques. The intermediate alcohol may be prepared by cyclisation of a compound of formula (III) wherein Q is a hydroxyl group (or a protected derivative thereof) using standard conditions.

Compounds of general formula (I) may also be prepared by another general process (D) which comprises reducing a compound of general formula (VII):

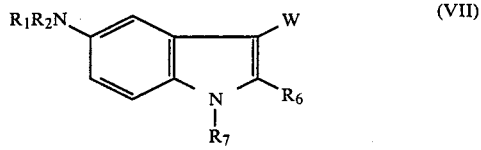

wherein W is a group capable of being reduced to give the required AlkNR$_4$R$_5$ group or a protected derivative thereof or a salt or protected derivative thereof.

The required Alk and NR$_4$R$_5$ groups may be formed by reduction steps which take place separately or together in any appropriate manner.

Groups which may be reduced to the group Alk include corresponding unsaturated groups and corresponding groups containing either a hydroxyl group or a carbonyl function.

Groups which may be reduced to the group NR$_4$R$_5$ where R$_4$ and R$_5$ are both hydrogen include nitro, azido, hydroxyimino and nitrile groups. Reduction of a nitrile group yields the group CH$_2$NH$_2$ and thus provides a methylene group of the group Alk.

The required NR$_4$R$_5$ groups wherein R$_4$ and/or R$_5$ are other than hydrogen may be prepared by reduction of a nitrile (CHR$_{11}$)$_x$CHR$_{12}$CN or an aldehyde (CHR$_{11}$)$_x$CHR$_{12}$CHO (where R$_{11}$ and R$_{12}$, which may be the same or different, each represents a hydrogen atom or a C$_{1-3}$ alkyl group and x is zero or 1) in the presence of an amine, R$_4$R$_5$NH. Alternatively the R$_4$R$_5$NH group may be prepared by reaction of the corresponding compound wherein R$_4$ and/or R$_5$ represent hydrogen with an appropriate aldehyde or ketone in the presence of a suitable reducing agent. In some instances (e.g for the introduction of the group R$_5$ where R$_5$ is benzyl) the aldehyde (e.g. benzaldehyde) may be condensed with the amine and the intermediate thus formed may subsequently be reduced using a suitable reducing agent.

Examples of groups represented by the substituent group W include the following: THO$_2$ (where T is Alk or an alkenyl group corresponding to the group Alk); AlkN$_3$; (CHR$_{11}$)$_x$CHR$_{12}$CN; COCHR$_{12}$Z; (CHR$_{11}$)$_x$CR$_{12}$=NOH; or CH(OH)CHR$_{12}$NR$_4$R$_5$ (where R$_{11}$, R$_{12}$ and x are as previously defined and Z is an azido group N$_3$ or the group NR$_4$R$_5$ or a protected derivative thereof).

It will be appreciated that the choice of reducing agent and reaction conditions will be dependent on the nature of the group W and other groups already present on the molecule.

Suitable reducing agents which may be used in the above process include hydrogen in the presence of a metal catalyst (except wherein R$_1$ is the group CSNR$_9$R$_{10}$), an alkali metal borohydride or cyanoborohydride, e.g. sodium borohydride or cyanoborohydride (except wherein W contains a nitrile or hydroxyimino group) or a metal hydride, e.g. lithium aluminium hydride (wherein R$_1$ is the group CSNR$_9$R$_{10}$ and one of R$_2$, R$_9$ and R$_{10}$ is hydrogen).

The metal catalyst may, for example be Raney Nickel or a noble metal catalyst, such as platinum, platinum oxide, palladium or rhodium, which may be supported, for example, on charcoal or kieselguhr. In the case of Raney nickel, hydrazine may also be used as the source of hydrogen.

Reduction in the presence of hydrogen and a metal catalyst may conveniently be carried out in a solvent such as an alcohol e.g. ethanol, an ether e.g. dioxan or tetrahydrofuran or an ester e.g. ethyl acetate at a temperature of from −10° to +50° C., preferably −5° to +30° C. The alkali metal borohydride or cyanoborohydride reduction may conveniently be carried out in an alcohol such as propanol or ethanol and at a temperature of from 0° to 100° C. In some instances the borohydride reduction may be carried out in the presence of cobaltous chloride. The metal hydride reduction may be carried out using an ether, e.g. tetrahydrofuran as solvent and conveniently at a temperature of from $-10°$ to $+100°$ C.

Particular embodiments of this process include the reduction of a compound of formula (VII) wherein W is the group $CHR_{12}CN$, $CHR_{11}CHR_{12}NO_2$, $CH=CR_{12}NO_2$ or $CHR_{11}CR_{12}=NOH$, for example, by catalytic reduction with hydrogen, e.g. hydrogen in the presence of a catalyst such as palladium, optionally in the presence of a mineral acid such as hydrochloric or sulphuric acid.

A second embodiment of the process involves, for example, the reduction of a compound of formula (VII) wherein W is the group $CHR_{12}CN$ in the presence of an amine $HNR_4R_5$ using hydrogen in the presence of a catalyst such as palladium, except that $R_1$ may not be $-CSNR_9R_{10}$.

According to a third embodiment, a compound of formula (VII) wherein W is the group $COCHR_{12}Z$ may be reduced, preferably with heating, using for example, sodium borohydride in propanol. Where Z is an azido group, the process results in the formation of a compound of general formula (I) wherein $R_4$ and $R_5$ are both hydrogen atoms.

According to a fourth embodiment, a compound of formula (VII) wherein W is the group $AlkN_3$ or $CH(OH)CHR_{12}NR_4R_5$ may be reduced using for example hydrogen in the presence of a catalyst (e.g. palladium) or sodium borohydride. These reducing agents are also suitable for the reductive alkylation of for example $AlkNHR_5$ in the presence of a suitable aldehyde or ketone.

The starting materials or intermediate compounds of general formula (VII) may be prepared by analogous methods to those described in UK Published Pat. Application No. 2035310 and "A Chemistry of Heterocyclic Compounds-Indoles Part II", Chapter VI, edited by W. J. Houlihan (1972) Wiley Interscience, NY.

Compounds of formula (VII) wherein W is the group $(CHR_{11})_xCHR_{12}CHO$ may be prepared by oxidation (e.g. with Jones' reagent) of a compound of general formula (VI) wherein Y is a hydroxyl group. A compound of general formula (VII) wherein W is the group $(CHR_{11})_xCR_{12}=NOH$ may be prepared by treatment of the corresponding aldehyde with hydroxylamine hydrochloride using standard conditions.

The intermediate compound of general formula (VII) wherein W is the group $AlkN_3$ may be prepared from a compound of general formula (VI) wherein Y is a halogen atom using standard procedures.

Standard reducing agents such as sodium borohydride may be used to prepare a compound of general formula (VII) wherein W is the group $CH(OH)CHR_{12}NR_4R_5$ from the corresponding compound of formula (VII) wherein W is the group $COCHR_{12}NR_4R_5$.

The following reactions (E), in any appropriate sequence, may if necessary and/or desired, be carried out subsequent to any of the above described processes:

(i) conversion of one compound of general formula (I) or a salt or protected derivative thereof into another compound of general formula (I);

(ii) removal of any protecting groups, and (iii) conversion of a compound of general formula (I) or a salt thereof into a physiologically acceptable salt, solvate (e.g. hydrate) or bioprecursor thereof.

Thus, a compound formula (I) according to the invention may be converted into another compound of the invention using conventional procedures.

For example, a compound of general formula (I) wherein $R_2$, $R_4$, $R_5$ and/or $R_7$ are alkyl groups may be prepared from the corresponding compounds of formula (I) wherein one or more of $R_2$, $R_4$, $R_5$ and $R_7$ represent hydrogen, by reaction with a suitable alkylating agent such as an alkyl halide, alkyl tosylate or dialkylsulphate. The alkylation reaction is conveniently carried out in an inert organic solvent such as an amide (e.g. dimethylformamide) an ether (e.g. tetrahydrofuran) or an aromatic hydrocarbon (e.g. toluene) preferably in the presence of a base. Suitable bases include, for example, alkali metal hydrides, for example sodium hydride, alkali metal amides, such as sodium amide, alkali metal carbonates, such as sodium carbonate or an alkali metal alkoxide such as sodium or potassium methoxide, ethoxide or t-butoxide.

A particularly suitable method for preparing a compound formula (I) wherein $R_4$ and/or $R_5$ is other than hydrogen, is reductive alkylation of the corresponding compound wherein $R_4$ and/or $R_5$ represents hydrogen, with an appropriate aldehyde or a ketone (e.g. benzaldehyde or acetone) in the presence of a suitable reducing agent. Alternatively the aldehyde or ketone may be condensed with the primary amine and the intermediate thus formed may subsequently be reduced using a suitable reducing agent.

It will be appreciated that the choice of reducing agents and reaction conditions depends upon the nature of the substituent groups already present on the compound of formula (I) which is to be alkylated. Suitable reducing agents which may be employed in this reaction include hydrogen in the presence of a metal catalyst, an alkali metal borohydride or cyanoborohydride (e.g. sodium borohydride or cyanoborohydride) using the conditions previously described or formic acid (using the carbonyl compound as reaction solvent, at a temperature of from $0°-100°$ C., conveniently $0°-50°$ C.)

According to a further embodiment, a compound of general formula (I) where $R_5$ is a hydrogen atom, may be prepared by reduction of a corresponding compound of general formula (I) wherein $R_5$ is a benzyl group, for example with hydrogen in the presence of a catalyst e.g. 10% palladium on carbon.

It should be appreciated that in some of the above transformations it may be necessary or desirable to protect any sensitive groups in the molecule of the compound in question to avoid any undesirable side reactions. For example, during any of the reaction sequences described above, it may be necessary to protect the group $NR_4R_5$, wherein $R_4$ and/or $R_5$ represent hydrogen, with a group easily removable at the end of the reaction sequence. Such groups may include, for example, aralkyl groups, such as benzyl, diphenylmethyl or triphenylmethyl; or acyl groups, such as N-benzyloxycarbonyl or t-butoxycarbonyl or phthaloyl.

In some cases, it may also be necessary to protect the indole nitrogen wherein $R_7$ is hydrogen.

Subsequent cleavage of the protecting group may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

Where it is desired to isolate a compound of the invention as a salt, for example as an acid addition salt, this may be achieved by treating the free base of general formula (I), with an appropriate acid, preferably with an equivalent amount or with creatinine sulphate in a suitable solvent (e.g. aqueous ethanol).

The starting materials or intermediate compounds for the preparation of the compounds according to this invention may be prepared by analogous methods to those described in UK Published Pat. Application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced either before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following examples. All temperatures are in °C.

Preparation 1

N-[3-(Cyanomethyl)-1H-indol-5-yl]formamide

A solution of 5-amino-1H-indole-3-acetonitrile (0.5 g) in methyl formate (20 ml) was stirred at room temperature for 24 h. The resulting solid precipitate was filtered off, washed with ether (2×20 ml) and dried in vacuo to give the title compound (0.41 g) as a white microcrystalline solid m.p. 196°6–200° (softens 194°).

Preparation 2

5-(Methylamino)-1H-indole-3-acetonitrile, quarter hydrate

A solution of 5-amino-1H-indole-3-acetonitrile (3.6 g) in triethyl orthoformate (80 ml) containing trifluoroacetic acid (3 drops) was refluxed for 24 h. The solvent was evaporated in vacuo and the residue was dissolved in absolute ethanol (50 ml), cooled to 0° C., treated with excess sodium borohydride (4.5 g) and then refluxed for 5 h.

The cooled solution was then added to a mixture of 2N hydrochloric acid (400 ml) and ice, washed with ethyl acetate (2×100 ml) and the acid solution was then basified (Na$_2$CO$_3$) and extracted with ethyl acetate (2×200 ml). These combined extracts were dried (Na$_2$SO$_4$), filtered, and the solvent was evaporated in vacuo yielding a brown oil. Column chromatography (Kieselgel 60, 250 g) eluting with ether afforded the title compound as a fawn solid (1.5 g) m.p. 120°–2°.

Preparation 3

2-[2-[5-(Aminomethyl)-1H-indol-3-yl]ethyl]-1H-isoindole-1,3(2H)-dione, hemisulphate, hydrate A suspension of 3-[2-(1,3-dihydro-1,3-dioxo-2H-isoiondol-2-yl)ethyl]-1H-indole-5-carbonitrile (4.7 g) in methanol (250 ml) and sulphuric acid (1.5 ml) was hydrogenated at room temperature and pressure over 10% palladium on charcoal (50% aqueous paste; 2.0 g) for 45 h. The catalyst was filtered off, and the filtrate was evaporated to dryness, giving an orange oil, which was dissolved in hot water (70 ml). On cooling, the title compound crystallised as a cream solid (3.8 g) m.p. 235°–8°.

Preparation 4

Phenylmethyl [2-[5-(aminomethyl)-1H-indol-3-yl]ethyl]carbamate (i) Phenylmethyl [2-[5-(hydroxymethyl)-1H-indol-3-yl]ethyl]-carbamate A solution of 3-[2-[[(phenylmethoxy)carbonyl]amino]ethyl]-1H-indole-5-carboxylic acid (9 g) and carbonyldiimidazole (5.2 g) in dry tetrahydrofuran (THF) (150 ml) was stirred vigorously under nitrogen at room temperature for 5 h. A solution of lithium borohydride (1.6 g) in dry THF (70 ml) was added over 70 min and the mixture then stirred for 18 h. Aqueous acetic acid (30%, 25 ml) was added slowly to the ice-cooled mixture and the solution was then partitioned between brine (25%, 300 ml) and ethyl acetate (250 ml). The organic layer was washed with sulphuric acid (0.4M, saturated with sodium chloride, 3×80 ml), brine (100 ml) and potassium carbonate solution (25%, 2×100 ml). The dried (MgSO$_4$) solution was evaporated in vacuo, the residue taken up in dichloromethane (150 ml) and insoluble material was filtered off. The filtrate was evaporated in vacuo to leave the alcohol (9 g) as a colourless oil containing some (ca. 45 mole %) ethyl acetate. T.l.c. Si0$_2$/Et$_2$O, R$_f$0.25.

(ii) Phenylmethyl [2-[5-(aminomethyl)-1H-indol-3-yl]ethyl]-carbamate

A solution of diethyl azodicarboxylate (1.48 g) in dry tetrahydrofuran (THF) (8 ml) was added over 2 min., keeping the temperature at 25°, to a stirred solution of phenylmethyl [2-[5-(-hydroxymethyl)-1H-indol-3-yl]ethyl]-carbamate (2.6 g), triphenylphosphine (2.35 g) and phthalimide (1.75 g) in THF (20 ml). After 4 h, the solvent was evaporated in vacuo and the residue was dissolved in a solution of hydrazine hydrate (15 ml) in ethanol (100 ml).

After 5 days the mixture was partitioned between sulphuric acid (0.5N, 500 ml) and ethyl acetate (2×300 ml). The acid layer was basified with potassium carbonate and the product was extracted into ethyl acetate (200 ml). The dried (Na$_2$SO$_4$) extract was evaporated in vacuo to leave the crude amino (0.7 g) as a brown oil which later solidified. Crystallisation from ethyl acetate gave the title compound (0.15 g) as cream coloured crystals m.p. 125.5°–.26.5°.

Example 1

Ethyl [3-(2-Aminoethyl)-1H-indol-5-yl] carbamate, compound with creatinine, sulphuric acid and water (2:2:2:1)

(i) Ethyl [3-(cyanomethyl)-1H-indol-5-yl] carbamate

A solution of 5-amino-1H-indole-3-acetonitrile (1.5 g) in dimethyl-formamide (35 ml) was treated with potassium carbonate (4.2 g) and ethyl chloroformate (0.9 ml) added dropwise over 20 min. After a further 5 min, the reaction mixture was poured into water (150 ml), left for 30 min and then extracted with ethyl acetate (3×130 ml). The combined ethyl acetate extracts were washed with water (2×150 ml), 8% sodium bicarbonate solution (2×150 ml) and water (2×100 ml) and dried (MgSO$_4$) and the solvent was removed under reduced pressure to afford a brown oil. The oil was crystallised from ethyl acetate and cyclohexane to give the title compound (1.65 g) as a brown crystalline solid, m.p. 119°–123°.

(ii) Ethyl [3-(aminoethyl)-1H-indol-5-yl]carbamate, compound with creatinine, sulphuric acid and water (2:2:2:1)

Ethyl [3-(cyanomethyl)-1H-indol-5-yl]carbamate (1.5 g) was catalytically hydrogenated over 5% rhodium-on-alumina (0.5 g) in a mixture of ethanol (50 ml) and ammonia (0.6 ml) for 40 h at 40° then at 50° for a further 8 h. The mixture was filtered through hyflo and evaporated to dryness to afford a brown oil. This oil was purified by column chromatography on silica (25 g) using ethyl acetate/2-propanol/water/ammonia (25:15:4:1) as eluant to give a brown oil (0.58 g) which was dissolved in ethanol and treated with an aqueous solution of creatinine and sulphuric acid (1:1, 2M, 1 ml) to give an off-white solid which was recrystallised from aqueous acetone to give the title compound as a colourless solid (0.65 g) m.p. 184.5°–187.5°.

Analysis. Found: C,43.4; H,5.9; N,17.65. $C_{13}H_{17}N_3O_2 \cdot C_4H_7N_3O \cdot H_2SO_4 \cdot 0.5H_2O$ requires: C,43.7; H,5.8; N,18.0%.

Example 2

N-[3-(2-Aminoethyl)-1H-indol-5-yl]formamide, compound with creatinine, sulphuric acid and water (1:1:1:1.3)

Hydrazine hydrate (30 ml) was added slowly over 3 h to a mixture of N-[3-(cyanomethyl)-1H-indol-5-yl]formamide (1.0 g) and Raney nickel (2 g) in ethanol (100 ml) at reflux under nitrogen. The catalyst was filtered off and the filtrate evaporated to an oil (1.1 g) which was dissolved in a hot mixture of ethanol (60 ml) and water (30 ml) and treated with a solution of creatinine sulphate (1.2 g) in water (4 ml). Dilution with ethanol (150 ml) precipitated the title compound as a white solid (1.4 g) m.p. 175°–183°.

Analysis. Found: C,41.5; H5.6 N,18.7. $C_{11}H_{13}N_3O \cdot C_4H_7N_3O \cdot H_2SO_4 \cdot 1.3H_2O$ requires: C,41.1; H,5.7; N,19.2%.

Example 3

N-[3-(2-Aminoethyl)-1H-indol-5-yl]-N-methylformamide, compound with creatinine, sulphuric acid and water (8:10:9:16)

(i) N-[3-(Cyanomethyl)-1H-indol-5-yl]-N-methylformamide

A solution of 5-(methylamino-1H-indole-3-acetonitrile (0.2 g) in methyl formate (7 ml) was kept at room temperature for 36 h. The solvent was evaporated in vacuo and the residue was partitioned between ethyl acetate (10 ml) and hydrochloric acid (2N, 10 ml). The organic layer was dried (Na2SO4) and evaporated in vacuo yielding the title compound as a fawn solid, (0.13 g) m.p. 118°–120° C.

(ii) N-[3-(2-Aminoethyl)-1H-indol-5-yl]-N-methylformamide compound with creatinine, sulphuric acid and water (8:10:9:16)

Following the method described in Example 2, N-[3-(cyanomethyl)-1H-indol-5-yl]-N-methylformamide (1.2 g) in ethanol (150 ml) was reduced with Raney nickel (0.03 g) and hydrazine hydrate (23 ml) over 8 h. The title compound (1.4 g) was obtained as a buff solid m.p. 208°–210° after creatinine sulphate formation.

Analysis. Found: C,40.8; H,5.6; N,18.7. $C_{12}H_{15}N_3O \cdot 1.25C_4H_7N_3O \cdot 1.125H_2SO_4 \cdot 2H_2O$ requires: C,40.4; H,6.0; N,18.7%.

Example 4

Ethyl [3-(2-aminoethyl)-1H-indol-5-yl]methylcarbamate, compound with creatinine sulphuric acid and water (1:1:1:2)

(i) Ethyl [3-(cyanomethyl)-1H-indol-5-yl]methylcarbamate

Ethyl chloroformate (0.21 ml) was added dropwise to a stirred solution of 5-(methylamino)-1H-indole-3-acetonitrile (0.4 g) in dimethylformamide (15 ml). After 10 min. the solution was diluted with water (30 ml), stirred for 30 min. and extracted with ethyl acetate (2×100 ml). The combined extracts were washed with 10% brine (2×100 ml), 8% sodium bicarbonate (2×100 ml) and water (2×100 ml), dried (Na2SO4) and evaporated in vacuo to yield the crude product as a brown oil. Trituration with ether gave a fawn solid (0.4 g). A sample was crystallised from ether to give the title compound as a white solid m.p. 104°–106°.

(ii) Ethyl [3-(2-aminoethyl)-1H-indol-5-yl]methylcarbamate, compound with creatinine, sulphuric acid, and water (1:1:1:2)

A solution of ethyl [3-(cyanomethyl)-1H-indol-5-yl]methylcarbamate (0.2 g) in absolute ethanol (30 ml) containing concentrated hydrochloric acid (8 drops) was hydrogenated at room temperature and pressure over palladium on charcoal (10%, 0.4 g) until hydrogen uptake ceased (8 h, 23 ml). The catalyst was filtered off, washed with absolute ethanol, and the filtrate evaporated in vacuo yielding a brown oil. The amine was dissolved in a hot solution of ethanol and water (8:1, 18 ml) and treated with an aqueous solution of creatinine and sulphuric acid (1:1, 2M, 0.38 ml). Filtration of the cooled mixture gave the title compound as a white solid m.p. 210°–212° (dec.) (0.15 g).

Analysis. Found: C,42.7; H,5.9; N,16.7. $C_{14}H_{19}N_3O_2 \cdot C_4H_7N_3O \cdot H_2SO_4 \cdot 2H_2O$ requires: C,42.5; H,6.3; N,16.5%.

Example 5

N-[3-(2-Aminoethyl)-1H-indol-5-yl]urea, compound with creatinine, sulphuric acid and water (1:1:1:1)

(i) N-[3-(Cyanomethyl)-1H-indol-5-yl]urea

A solution of sodium cyanate (1.2 g) in water (10 ml) was added to a stirred solution of 5-amino-1H-indole-3-aceto-nitrile (1.5 g) in glacial acetic acid (5 ml) and water (10 ml). Stirring was continued until a brown gum precipitated (10 min). The aqueous layer was then decanted off, and extracted with ethyl acetate (2×100 ml). The combined extracts were washed with sodium carbonate soln. (2N, 2×100 ml), dried (Na2SO4) and evaporated in vacuo to yield the crude urea as an off-white solid (0,3 g). The brown gum was purified by column chromatography (Kieselgel 60, 25 g) using ethyl acetate as eluant to yield more of the crude urea (0.1 g). The crude urea was then crystallised from isopropanol to yield the title compound as a fawn solid (0.3 g) m.p. 200°–204°.

(ii) N-[3-(2-Aminoethyl)-1H-indol-5-yl]urea, compound with creatinine, sulphuric acid and water (1:1:1:).

Following the method of Example 2, N-[3-(cyanomethyl)-1H-indol-5-yl]urea (0.2 g) in ethanol (30 ml) was reduced with Raney nickel (0.03 g) and hydrazine hydrate (6 ml) over 5 h. The title compound (0.15 g) was obtained as a cream solid m.p. 208°–12° after creatinine sulphate formation.

Analysis. Found: C,40.1; H,5.6; N,21.5; $C_{11}H_{14}N_4O.C_4H_7N_3O.H_2SO_4.H_2O$. requires: C,40.3; H,5.6; N,21.9%.

T.l.c. Silica ethyl acetate/2-propanol/water/0.88 amonia (25:15:8:2) $R_f 0.44$.

Example 6

Methyl[3-(2-aminoethyl)-1H-indol-5-yl]carbamate, compound with creatinine, sulphuric acid and water (1:1:1:1).

(i) Methyl[3-(cyanomethyl)-1H-indol-5-yl]carbamate

Following the method of Example 4(i), 5-amino-1H-indole-3-acetonitrile (0.8 g) in dimethylformamide (10 ml) was reacted with methyl chloroformate (0.5 ml) to give the title compound (0.44 g) as a white solid m.p. 146°–8° after column chromatography (Kieselgel 60, 100 g) eluted with ether.

(ii) Methyl [3-(2-aminoethyl)-1H-indol-5-yl]carbamate, compound with creatinine, sulphuric acid, and water (1:1:1:1)

Following the method of Example 4 (ii) methyl[3-(cyanomethyl)-1H-indol-5-yl]carbamate (0.7 g) was hydrogenated in ethanol (100 ml) over palladium on charcoal (10%, 1.0 g) for 24 h to give, after creatinine sulphate formation, the title compound (0.5 g) as a white solid m.p. 197°–200°.

Analysis. Found: C,41.4; H,5.7; N,18.1. $C_{12}H_{15}N_3O_2.C_4H_7N_3O.H_2SO_4.H_2O$ requires: C,41.55; H,5.7; N.18.2%.

Example 7

N-[3-[2-(Methylamino)ethyl]-1H-indol-5yl]formamide, compound with creatinine, sulphuric acid and water (10:12:11:20)

A solution of N-[3-(cyanomethyl)-1H-indol-5-yl]formamide (0.3 g) in absolute ethanol (30 ml) containing methylamine, (33% in ethanol, 2 ml) was hydrogenated at room temperature and pressure over palladium oxide on charcoal (10%, 0.5 g) for 24 h until hydrogen uptake ceased (90 ml). The catalyst was filtered off, washed with absolute ethanol, and the filtrate was evaporated in vacuo yielding a brown oil.

The amine was dissolved in a hot mixture of ethanol and water (8:1, 18 ml) and an aqueous solution of creatinine and sulphuric acid (1:1, 2M, 0.6 ml) was added. Filtration of the cooled mixture gave the title compound as an off-white solid (0.35 g) m.p. 205°–207°.

Analysis. Found: C,40.6; H,5.5; N,.18.8. $C_{12}H_{15}N_3O.1.2C_4H_7N_3O.1.1H_2SO_4.2H_2O$ requires: C,40.7; H,5.8; N.18.6%.

Example 8

N-[3-(2-Aminoethyl)-1H-indol-5-yl]acetamide, compound with creatinine, sulphuric acid and water (2:3:2:5)

(i) N-[3-(Cyanomethyl)-1H-indol-5-yl]acetamide

Acetyl chloride (0.21 ml) was added dropwise to a stirred solution of 5-amino-1H-indole-3-acetonitrile (0.5 g) and pyridine (0.24 ml) in dry acetonitrile (10 ml) at 0°–2° under nitrogen. When the addition was complete the solution was stirred at 0° for 30 minutes, poured into water (50 ml) and extracted with ethyl acetate (3×25 ml). The combined extracts were dried (MgSO$_4$), filtered and evaporated under reduced pressure to a brown solid (0.5 g) which was crystallised from an ethanol-cyclohexane mixture to give the title compound (0.43 g) as off-white needles, m.p. 171.5°–175°.

(ii) N-[3(2-Aminoethyl)-1H-indol-5-yl]acetamide, compound with creatinine, sulphuric acid and water (2:3:2:5)

Following the method described in Example 2, N-[3-(cyanomethyl)-1H-indol-5-yl]acetamide (0.3 g) in ethanol (15 ml) was reduced with Raney nickel (0.06 g) and hydrazine hydrate (6.2 ml) over 6 h. The title compound was obtained as a white crystalline solid m.p. 177°–182°(dec).

Analysis. Found: C,40.6; H,5.7; N,20.1. $C_{12}H_{15}N_3O.1.5C_4H_7N_3O.H_2SO_4.2.5H_2O$: C,40.8; H,6.2; N,19.8%.

The following compounds were prepared according to the method described in Example 8(i) from 5-amino-1H-indole-3-acetonitrile and the appropriate acid chloride or acid anhydride as detailed in Table I.

Example 9

N-[3-(2-Aminoethyl)-1H-indol-5-yl]-2-methylpropanamide, compound with hydrogen chloride and water (4:4:3)

(ii) A solution of N-[3-(cyanomethyl)-1H-indol-5-yl]-2-methylpropanamide (0.4 g) in absolute ethanol (50 ml) containing concentrated hydrochloric acid (10 drops) was hydrogenated at room temperature and pressure over palladium on charcoal (10%. 1.5 g) for 16 h, before the catalyst was replaced (10%, 1 g). After a further 4 h, when hydrogen uptake (75 ml) had ceased, the catalyst was

TABLE I

| Ex. No. | Wt. of starting material (g) | Reagent | Vol. of Reagent (ml) | Vol. of pyridine (ml) | Vol. of CH$_3$CN (ml) | Wt. of product (g) | Recrystallisation solvent | Mol. formula | m.p. (°C.) |
|---|---|---|---|---|---|---|---|---|---|
| 9 (i) | 2.8 | Pr$^i$COCl | 1.8 | 2 | 50 | 1.8 | * | C$_{14}$H$_{15}$N$_3$O | 138–140 |
| 10 (i) | 2.0 | (CF$_3$CO)$_2$O | 2.45 | 1 | 40 | 1.46 | Ethyl acetate/cyclohexane | C$_{12}$H$_8$F$_3$N$_3$O | 165–6 |

*Purified by column chromatography on Kieselgel 60 (150 g) eluted with ethyl acetate , filtered off, washed with absolute ethanol, and the filtrate was evaporated in vacuo yielding a brown solid. The crude hydrochloride was crystallised from a mixture of methanol and ethyl acetate, to give the title compound as a light brown solid (0.2 g) m.p. 274°–276°.

Analysis. Found: C,56.7; H,7.4; N,13.7. $C_{14}H_{19}N_3O.HCl.0.75H_2O$ requires: C,56.95; H,7.3; N,14.2%.

Example 10

N-[3-(2-Aminoethyl)-1H-indol-5-yl]trifluoroacetamide, compound with creatinine, sulphuric acid and water (1:1:1:2)

(ii) N-[3-(Cyanomethyl)-1H-indol-5-yl]trifluoroacetamide (1.3 g) in ethanol (50 ml) and ammonia (0.6 ml) was hydrogenated at room temperature and pressure over rhodium-on-alumina (0.5 g) for 48 h. The mixture was filtered through hyflo and evaporated to dryness under reduced pressure to afford a brown oil. The brown oil was purified by column chromatography (Kieselgel 60, 25 g) using a mixture of ethyl acetate, 2-propanol, water and ammonia (25:15:4:1) as eluent. The resulting solid was dissolved in hot ethanol and treated with an aqueous solution of creatinine and sulphuric acid (2M, 1:1, 1 ml) and the resulting solid was recrystallised from aqueous acetone to give the title compound as a pinkish solid m.p. 186°–215° (dec).

Analysis. Found: C,37.2; H,5.05; N,16.2. $C_{12}H_{12}F_3N_3O.C_4H_7N_3O.H_2SO_4 2H_2O$ requires: C,37.1; H,4.9; N,16.2%.

Example 11

N-[3-(2-Aminoethyl)-1H-indol-5-yl]-N'-methylthiourea, compound with creatinine, sulphuric acid and water (1:1:1:1)

(i) N-[3-(Cyanomethyl)-1H-indol-5-yl]N'-methylthiourea, compound with ethanol (2:1)

Methyl isothiocyanate (0.40 ml) was added to a stirred solution of 5-amino-1H-indole-3-acetonitrile (1 g) in dry acetonitrile (20 ml). The solution was stirred at room temperature for 3 days. A further quantity of methyl isothiocyanate (0.05 ml) was added and the mixture was heated at 50° for 5 h. The solution was evaporated in vacuo to a viscous oil which solidified on trituration with an ethanolether mixture. The resulting solid was filtered off and dried in vacuo to give the title compound (1.17 g) as an off-white crystalline solid, m.p. 103°–110°.

(ii) N-[3-(2-Aminoethyl)-1H-indol-5-yl]-N'-methylthiourea, compound with creatinine, sulphuric acid and water (1:1:1:1)

Lithium aluminium hydride (0.19 g) was added in small portions at 18°–20° to a stirred suspension of N-[3-(cyanomethyl)-1H-indol-5-yl]-N'-methylthiourea (0.4 g) in dry tetrahydrofuran (10 ml) under nitrogen. When the addition was complete the yellow suspension was heated at reflux for 2 h. The suspension was cooled to room temperature and the excess lithium aluminium hydride was destroyed by the careful addition of a water-ethanol mixture (1:1) (30 ml). The resulting suspension was filtered off and the filtrate was evaporated under reduced pressure to a yellow semi-solid. Ethanol (50 ml) and water (10 ml) were added to the solution was filtered to remove a small quantity of insoluble material. The filtrate was heated to reflux and treated with a hot solution of creatinine sulphate (0.6 g) in water (2 ml). On cooling, the title compound was obtained as a buff-coloured solid m.p. 226°–9° (dec).

Analysis. Found: C,40.3; H,5.5; N,20.1. $C_{12}H_{16}N_4S.C_4H_7N_3O.H_2SO_4.H_2O$ requires: C,40.2; H,5.7; N,20.5%.

Example 12

N-[3-(2-Aminoethyl)-1H-indol-5-yl]thiourea, fumarate, hemihydrate (i) Ethyl [[[3-(cyanomethyl)-1H-indol-5-yl]amino]thiocarbonyl]carbamate Ethoxycarbonyl isothiocyanate (1.2 ml) was added dropwise to a stirred solution of 5-amino-1H-indole-3-acetonitrile (1.7 g) in dry acetonitrile (50 ml). After 10 min. the resulting suspension was diluted with water (40 ml) and stirred for 20 min.

The precipitate was filtered off, washed with dry acetonitrile, and dried in vacuo to give the title compound as a cream solid (1.5 g) m.p. 201°–202 °C.

(ii) N-[3-(Cyanomethyl)-1H-indol-5-yl]thiourea

A solution of ethyl [[[3-(cyanomethyl)-1H-indol-5-yl]amino]thiocarbonyl]carbamate (0.5 g) in 2N sodium hydroxide (3 ml) and ethanol (10 ml) was stirred at 40° C. for 2 h. The resulting precipitate was filtered off, triturated with water (40 ml), washed with ethanol (ca. 30 ml) and dried in vacuo to give the title compound as a white solid. (0.25 g) m.p. 212°–214°C.

(iii) N-[3-(2-Aminoethyl)-1H-indol-5-yl]thiourea, fumarate, hemihydrate

Lithium aluminium hydride (0.5 g) was added portion-wise, under nitrogen, to a stirred suspension of N-[3-(cyanomethyl)-1H-indol-5-yl]thiourea (0.6 g) in THF (150 ml). When the addition was complete aluminium chloride (1.74 g) was added, and the resulting grey suspension was stirred at reflux for 1 h.

The mixture was cooled in ice and excess reagent decomposed by cautious addition of 10% water in THF. Brine (100 ml) and ethyl acetate (100 ml) were added, insoluble material filtered off, and the aqueous layer extracted with ethyl acetate (100 ml).

The combined organic solutions were washed with brine (100 ml), dried ($Na_2SO_4$) and evaporated in vacuo to yield a pale yellow oil. The oil was dissolved in a solution of fumaric acid (0.3 g) in methanol fumarate precipitate by the addition of ethyl acetate (250 ml). The salt was crystallised from isopropanol and recrystallised from a mixture of methanol and ethyl acetate to give the title compound as a cream solid (0.15 g) m.p. 147°–150°.

Analysis. Found: C,50.1; H,5.4; N,15.8. $C_{11}H_{14}N_4S.C_4H_4O_4.0.5H_2O$ requires: C,50.1; H,5.3; N,15.6%.

Example 13

2-methylpropyl [3(2-aminoethyl)-1H-indol-5-yl]carbamate, hydrochloride (i) 2-Methylpropyl [3-(cyanomethyl-1H-indol-5-yl]carbamate, quarter hydrate Isobutyl chloroformate (1.5 ml) was added dropwise to a stirred solution of 5-amino-1H-indole-3-acetonitrile (1.7 g) in dry DMF (20 ml). After 10 min the solution was diluted with water (150 ml) and stirring continued for 30 min. The resulting solution was extracted with ethyl acetate (2×100 ml) and the combined extracts washed with brine (10%, 100 ml), water (100 ml), dried ($Na_2SO_4$) and evaporated in vacuo to yield the crude product as a brown oil. This was purified by column chromatography (Kieselgel 60, 100 g) using ether as the eluent, to give the title compound as a colourless gum (1.08 g) which darkened to a brown gum on storage. This material failed to crystallise from common organic solvents.

Analysis. Found: C,65.8; H,6.4; N,14.7. $C_{15}H_7N_3O_2.0.25H_2O$ requires: C,65.3; H,6.4; N,15.2%.

(ii) 2-Methylpropyl [3-(2-aminoethyl)-1H-indol-5-yl]carbamate, hydrochloride

A solution of 2-methylpropyl [3-(cyanomethyl)-1H-indol-5-yl]carbamate, quarter hydrate (0.5 g) in absolute ethanol (30 ml) containing concentrated hydrochloric acid (8 drops) was hydrogenated at room temperature and pressure over palladium on charcoal (10%, 1 g) for 24 h before the catalyst was replaced (10%, 0.5 g). After a further 4 h when hydrogen uptake ceased (90 ml) the catalyst was filtered off, washed with absolute ethanol, and the filtrate evaporated in vacuo giving a pink solid. The crude hydrochloride was crystallised from a mixture of methanol and ethyl acetate, to give the title compound as a white solid (0.15 g) m.p. 258°-260°.

Analysis. Found: C,57.7; H,7.0; N,13.1. $C_{15}H_{21}N_3O_2$.HCl requires: C,57.8; H,7.1; N, b 13.5%.

Example 14

N-[3-(2-Aminoethyl)-1H-indol-5-yl]-N',N'-dimethylsulphamide, maleate.

(i) N-[3-(Cyanomethyl)-1H-indol-5-yl]-N',N'-dimethylsulphamide

Dimethyl sulphamoyl chloride (1.2 ml) was added dropwise to a stirred solution 5-amino-1H-indole-3-acetonitrile (1.7 g) in dry dimethyl-formamide (50 ml) containing triethylamine (2.8 ml). After 3 h, the resulting suspension was diluted with water (20 ml) and stirred for 30min. The resulting solution was poured into water (100 ml) and extracted with ethyl acetate (2×100 ml). The combined organic extracts were washed with water (100 ml) and brine (2×100 ml), dried (Na$_2$SO$_4$) and evaporated in vacuo, to give a dark brown oil which was purified by column chromatography (Kieselgel 60, 100 g) eluted with ether/ethyl acetate, (9:1) to give the title compound as white solid (0.75 g) m.p. 147°-150°.

(ii) N-[3-(2-Aminoethyl)-1H-indol-5-yl]-N',N'-dimethylsulphamide, maleate

A solution of N-[3-(cyanomethyl)-1H-indol-5-yl]-N',N'-dimethylsulphamide (0.3 g) in absolute ethanol (50 ml) containing concentrated hydrochloric acid (6 drops) was hydrogenated at room temperature and pressure over palladium on charcoal (10%, 0.2 g) for 24 h before the catalyst was replaced (10%, 0.5 g). After a further 4 h, when hydrogen uptake ceased (60 ml) the catalyst was filtered off, washed with ethanol, and the filtrate evaporated in vacuo to give a brown oil. The oil was then partitioned between ethyl acetate (2×20 ml) and 2N sodium carbonate (10 ml), the combined organic extracts dried (Na$_2$SO$_4$) and evaporated in vacuo to give a fawn foam. The foam was dissolved in a solution of maleic acid (0.16 g) in methanol (4 ml) and the maleate precipitated by the addition of ethyl acetate (100 ml) and ether (150 ml). The salt was crystallised from a mixture of methanol and ethyl acetate to give the title compound (0.6 g) as a fawn solid m.p. 138°-142°.

Analysis. Found: C,48.3; H,5.5; N,13.8. $C_{12}H_{18}N_4O_2S.C_4H_4O_4$ requires: C,48.2; H,5.6; N,14.1%.

PHARMACEUTICAL EXAMPLES

Tablets

These may be prepared by direct compression or wet granulation. The direct compression method is preferred but may not be suitable in all cases as is dependent upon the dose level and physical characteristics of the active ingredient.

| A. Direct Compression | mg/tablet |
|---|---|
| Active ingredient | 10.0 |
| Microcrystalline Cellulose B.P.C. | 89.5 |
| Magnesium Stearate | 0.5 |
| | 100.0 |

The active ingredient is sieved through a 250 μm sieve, blended with the excipients and compressed using 6.0 mm punches. Tablets of other strengths may be prepared by altering the compression weight and using punches to suit.

| B. Wet Granulation | mg/tablet |
|---|---|
| Active ingredient | 10.0 |
| Lactose B.P. | 74.5 |
| Starch B.P. | 10.0 |
| Pregelatinised Maize Starch B.P. | 5.0 |
| Magnesium Stearate B.P. | 0.5 |
| Compression Weight | 100.0 |

The active ingredient is sieved through a 250 μm sieve and blended with the lactose, starch and pregelatinised starch. The mixed powders are moistened with purified water, granules are made, dried, screened and blended with the Magnesium Stearate. The lubricated granules are compressed into tablets as described for the direct compression formulae.

The tablets may be film coated with suitable film forming materials, e.g. methyl cellulose or hydroxypropyl methyl cellulose using standard techniques. Alternatively the tablets may be sugar coated.

| Capsules | mg/capsule |
|---|---|
| Active ingredient | 10.0 |
| *Starch 1500 | 89.5 |
| Magnesium Stearate B.P. | 0.5 |
| Fill Weight | 100.0 |

*A form of directly compressible starch supplied by Colorcon Ltd., Orpington, Kent.

The active ingredient is sieved through a 250 μm sieve and blended with the other materials. The mix is filled into No. 2 hard gelatin capsules using a suitable filling machine. Other doses may be prepared by altering the fill weight and if necessary changing the capsule size to suit.

| Syrup | mg/5 ml dose |
|---|---|
| Active ingredient | 10.0 |
| Sucrose B.P. | 2750.0 |
| Glycerine B.P. | 500.0 |
| Buffer | |
| Flavour | |
| Colour | as required |
| Preservative | |
| Distilled Water | 5.00 ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

| Suppositories | |
|---|---|
| Active ingredient | 10.0 mg |
| *Witepsol H15 to | 1.0 g |

*A proprietary grade of Adeps Solidus ph. Eur.

A suspension of the active ingredient in the matter Witepsol H15 is prepared and filled using a suitable machine into 1g size suppository moulds.

| Injection for Intravenous Administration | |
|---|---|
| | % w/v |
| Active ingredient | 0.20 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| INHALATION CARTRIDGES | |
|---|---|
| | mg/cartridge |
| Active ingredient micronised | 1.00 |
| Lactose B.P. | 39.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler (e.g. Glaxo Rotahaler).

| METERED DOSE PRESSURISED AEROSOL | | |
|---|---|---|
| | mg/metered dose | Per can |
| Active ingredient micronised | 0.500 | 120 mg |
| Oleic Acid B.P. | 0.050 | 12 mg |
| Trichlorofluoromethane B.P. | 22.25 | 5.34 g |
| Dichlorodifluoromethane B.P. | 60.90 | 14.62 g |

The active ingredient is micronised in a fluid energy mill to a fine particle size range. The Oleic Acid is mixed with the Trichlorofluoromethane at a temperature of 10°–15° C. and the micronised drug is mixed into this solution with a high shear mixer. The suspension is metered into aluminum aerosol cans and suitable metering valves, delivering a metered dose of 85 mg of suspension are crimped onto the cans and the Dichlorodifluoromethane is pressure filled into the cans through valves.

We claim:

1. A compound of formula (I):

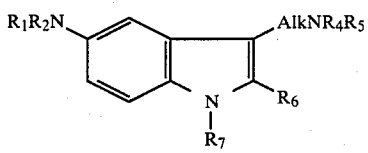

wherein $R_1$ represents a group CHO, $COR_8$, $CO_2R_8$, $CONR_9R_{10}$, $CSNR_9R_{10}$ or $SO_2NR_9R_{10}$, where $R_8$ represents $C_{1-6}$ alkyl optionally substituted by 1–3 halogen atoms; cyclo $C_{5-7}$ alkyl, phenyl, phenyl $C_{1-4}$ alkyl, wherein said phenyl groups are unsubstituted or substituted by one or more $C_{1-6}$ alkyl groups, halogen atoms, hydroxy or $C_{1-6}$ alkoxy groups;

$R_9$ represents a hydrogen atom or a $C_{1-6}$ alkyl group, and $R_{10}$ represents a hydrogen atom or a $C_{1-6}$ alkyl, cyclo $C_{5-7}$ alkyl, phenyl or phenyl $C_{1-4}$ alkyl group wherein said phenyl groups are unsubstituted or substituted by one or more $C_{1-6}$ alkyl groups, halogen atoms, hydroxy or $C_{1-6}$ alkoxy groups;

$R_2$, $R_4$, $R_6$ and $R_7$, which may be the same or different, each represents a hydrogen atom or a $C_{1-3}$ alkyl group;

$R_5$ represents a hydrogen atom or a $C_{1-6}$ alkyl, cyclo $C_{5-7}$ alkyl, $C_{3-6}$ alkenyl, or a phenyl $C_{1-4}$ alkyl group, wherein said phenyl group is unsubstituted or substituted by one or more $C_{1-6}$ alkyl groups, halogen atoms, hydroxy or $C_{1-6}$ alkoxy groups; and Alk represents an alkylene chain containing two or three carbon atoms which may be unsubstituted or substituted by not more than two $C_{1-3}$ alkyl groups;

with the provisos that when $R_4$ and $R_5$ both represent alkyl groups $R_1$ does not represent the group CHO or $COR_8$ and that when $R_4$, $R_5$, $R_6$ and $R_7$ all represent hydrogen $R_1$ does not represent the group $SO_2NH_2$; and physiologically acceptable salts and solvates thereof.

2. A compound according to claim 1, wherein Alk represents an unsubstituted alkylene chain containing two carbon atoms.

3. A compound according to claim 1, wherein $R_4$ and $R_5$, which may be the same or different, each represents a hydrogen atom or a methyl or ethyl group.

4. A compound according to claim 1, wherein $R_2$ represents a hydrogen atom or a methyl group.

5. A compound according to claim 1, having the formula (Ia):

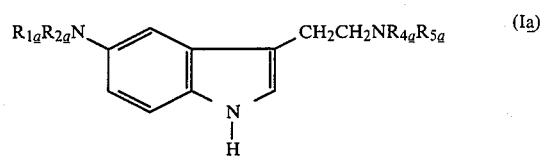

wherein $R_{1a}$ represents a group CHO, $CONH_2$, $COR_{8a}$ or $CO_2R_{8a}$, where $R_{8a}$ is an alkyl group containing 1 to 4 carbon atoms or a trifluoromethyl group;

$R_{2a}$ represents a hydrogen atom or a methyl group; and $R_{4a}$ and $R_{5a}$, which may be the same or different, each represents a hydrogen atom or a methyl or ethyl group with the provisos that the total number of carbon atoms in $R_{4a}$ and $R_{5a}$ together does not exceed two, that when $R_{1a}$ represents a group CHO or a group $COR_{8a}$ then $R_{4a}$ represents a hydrogen atom, and physiologically acceptable salts and solvates thereof.

6. A compound according to claim 1, having the formula (Ib):

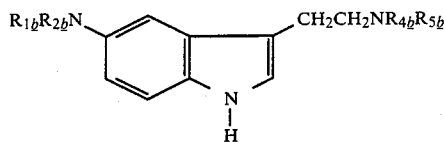

wherein $R_{1b}$ represents a group CHO, $CONH_2$ or $CO_2R_{8b}$ where $R_{8b}$ is a methyl, ethyl or isobutyl group;

$R_{2b}$ represents a hydrogen atom or a methyl group; and $R_{4b}$ and $R_{5b}$, which may be the same or different, each represents a hydrogen atom or a methyl or ethyl group with the provisos that the total number of carbon atoms in $R_{4b}$ and $R_{5b}$ together does not exceed two and that when $R_{1b}$ is the group CHO, $R_{4b}$ represents a hydrogen atom, and physiologically acceptable salts and solvates thereof.

7. A compound according to claim 1, wherein the physiologically acceptable salt is a hydrochloride, hydrobromide, sulphate, fumarate or a maleate.

8. A method of treating a patient suffering from migraine which comprises administering to the patient an effective amount of a compound of formula (I) as defined in claim 1 or a physiologically acceptable salt or solvate thereof.

9. A compound selected from the group consisting of ethyl [3-(2-aminoethyl)-1H-indol-5-yl]carbamate, 2-methylpropyl [3-(2-amino-ethyl)-1H-indol-5-yl]carbamate and physiologically acceptable salts and solvates thereof.

10. A pharmaceutical composition comprising an effective amount for the treatment of migraine of a compound of formula (I) of claim 1 or a physiologically acceptable salt or solvate thereof together with a physiologically acceptable carrier or excipient.

* * * * *